United States Patent
Silverman et al.

(10) Patent No.: US 6,291,526 B1
(45) Date of Patent: *Sep. 18, 2001

(54) GABA AND L-GLUTAMIC ACID ANALOGS FOR ANTISEIZURE TREATMENT

(75) Inventors: Richard B. Silverman, Morton Grove, IL (US); Ryszard Andruszkiewicz, Sopot (PL); Po-Wai Yuen, Ann Arbor, MI (US)

(73) Assignees: Northwestern University, Evanston, IL (US); Warner-Lambert Company, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/244,305

(22) Filed: Feb. 4, 1999

Related U.S. Application Data

(62) Division of application No. 08/899,918, filed on Jul. 24, 1997, now abandoned, which is a division of application No. 08/420,905, filed on Apr. 11, 1995, now Pat. No. 6,197,819, which is a continuation of application No. 08/064,285, filed on May 18, 1993, now abandoned, which is a continuation-in-part of application No. 07/886,080, filed on May 20, 1992, now abandoned, which is a continuation-in-part of application No. 07/618,692, filed on Nov. 27, 1990, now abandoned.

(51) Int. Cl.$^7$ .................................................. A61K 31/195
(52) U.S. Cl. ............................................................ 514/561
(58) Field of Search ................................................ 514/561

(56) References Cited

U.S. PATENT DOCUMENTS 4,322,440 * 3/1982 Fish ........................................ 514/561
5,563,175 * 10/1996 Silverman ............................. 514/561

FOREIGN PATENT DOCUMENTS 49-40460 * 11/1974 (JP).

* cited by examiner

*Primary Examiner*—Michael L. Shippen
(74) *Attorney, Agent, or Firm*—Kohn & Associates

(57) ABSTRACT

A compound of the formula

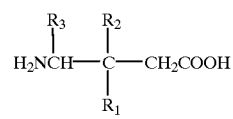

wherein $R_1$ is a straight or branched alkyl group having from 1 to 6 carbon atoms, phenyl, or cycloalkyl having from 3 to 6 carbon atoms; $R_2$ is hydrogen or methyl; and $R_3$ is hydrogen, methyl or carboxyl; which is useful in the treatment of seizure disorders. Processes are disclosed for the preparation of the compound. Intermediates prepared during the synthesis of the compound are also disclosed.

2 Claims, No Drawings

GABA AND L-GLUTAMIC ACID ANALOGS FOR ANTISEIZURE TREATMENT

CROSS REFERENCE TO RELATED APPLICATIONS

This application is a divisional of U.S. patent application Ser. No. 08/899,918, filed Jul. 24, 1997, now abandoned, which is a divisional of U.S. patent application Ser. No. 08/420,905, filed Apr. 11, 1995, now U.S. patent No. 6,197,819, which is a continuation of U.S. patent application Ser. No. 08/064,285, filed May 18,1993, abandoned, which is a continuation-in-part of U.S. patent application Ser. No. 07/886,080, filed May 20, 1992, abandoned, which is a continuation-in-part of U.S. patent application Ser. No. 07/618,692, filed Nov. 27, 1990, abandoned, all of which are incorporated herein by reference.

GRANT INFORMATION

This invention was made with Government support under Grant No. NS15703 awarded by the National Institutes of Health. The Government has certain rights in the invention.

TECHNICAL FIELD

The present invention relates to novel compounds that are analogs of glutamic acid and gamma-aminobutyric acid (GABA). More specifically, the analogs are useful as antiseizure therapy for central nervous system disorders such as epilepsy, Huntington's chorea, cerebral ischemia, Parkinson's disease, tardive dyskinesia, and spasticity. It is also possible that the present invention could be used as an antidepressant, anxiolytic, and antipsychotic activity.

BACKGROUND OF THE INVENTION

Gamma aminobutyric acid (GABA) and glutamic acid are two major neurotransmitters involved in the regulation of brain neuronal activity. GAHA is the major inhibitory neurotransmitter and L-glutamic acid is an excitatory transmitter (Roberts E, et al, *GABA in Nervous System Function*, Raven Press: New York, 1976; McGeer EG, et al, *Glutamine. Glutamate, and GABA in the Central Nervous System*; Hertz L, Kvamme E, McGeer EG, Schousbal A, eds., Liss: New York, 1983;3–17). An imbalance in the concentration of these neurotransmitters can lead to convulsive states. Accordingly, it is clinically relevant to be able to control convulsive states by controlling the metabolism of this neurotransmitter. When the concentration of GABA diminishes below a threshold level in the brain, convulsions result (Karlsson A, et al, *Biochem. Pharmacol* 1974;23:3053–3061). When the GABA levels rise in the brain during convulsions, seizures terminate (Hayashi T J, *Physiol*. (London) 1959;145:570–578). The term seizure as used herein means excessive unsynchronized neuronal activity that disrupts normal neuronal function. In several seizure disorders there is concomitant with reduced brain GABA levels a diminished level of L-glutamic acid decarboxylase (GAD) activity also observed (McGeer PO, et al, In: *GABA in Nervous System Function*; Roberts E, Chase TN, Tower DB, eds., Raven Press: New York 1976:487–495; Butterworth J, et al, *Neurochem*. 1983;41:440–447; Spokes EG, *Adv. Exp. Med. Biol*. 1978;123:461–473; Wu JY, et al, *Neurochem. Res*. 1979;4:575–586; and Iversen LL, et al, *Psychiat. Res*. 1974;11:255–256). Often, the concentrations of GAD and GABA vary in parallel because decreased GAD concentration results in lower GABA production.

Because of the importance of GABA as an inhibitory neurotransmitter, and its effect on convulsive states and other motor dysfunctions, a variety of approaches have been taken to increase the brain GABA concentration. For example, the most obvious approach was to administer GABA. When GABA is injected into the brain of a convulsing animal, the convulsions cease (Purpura DP, et al, *Neurochem*. 1959;,:238–268). However, if GABA is administered systematically, there is no anticonvulsant effect because GABA, under normal circumstances, cannot cross the blood brain barrier (Meldrum B S, et al, *Epilepsy*; Harris P, Mawdsley C, eds., Churchill Livingston: Edinburg 1974:55. In view of this limitation, there are three alternative approaches that can be taken to raise GABA levels.

The most frequent approach is to design a compound that crosses the blood brain barrier and then inactivates GABA aminotransferase. The effect is to block the degradation of GABA and thereby increase its concentration. Numerous mechanism-based inactivators of GABA aminotransferase are known (Silverman RB, *Mechanism-Based Enzyme Inactivation: Chemistry and Enzymolocy*, Vol. I and Il, CRC: Boca Raton 1988).

Another approach is to increase GABA concentrations in the brain by making GABA lipophilic by conversion to hydrophobic GABA amides (Kaplan JP, et al, *G.J. Med. Chem*. 1980;23:702–704; Carvajal G, et al, *Biochem. Pharmacol*. 1964;13:1059–1069; Imines: Kaplan JP, Ibid.; or GABA esters: Shashoua VE, et al, *J. Med. Chem*. 1984;27:659–664; and PCT Patent Application WO85/00520, published Feb. 14, 1985) so that GABA can cross the blood brain barrier. Once inside the brain, these compounds require amidase and esterases to hydrolyze off the carrier group and release GABA.

Yet another approach is to increase 25 brain GABA levels by designing an activator of GAD. A few compounds have been described as activators of GAD. The anticonvulsant agent, maleicimid, was reported to increase the activity of GAD by 11% and as a result increase GABA concentration in the substantia nigra by up. to 38% (Janssens de Varebeke P, et al, *Biochem. Pharmacol*. 1983;32:2751–2755. The anticonvulsant drug sodium valproate (Loscher W, *Biochem. Pharmacol*. 1982;31:837–842; Phillips N I, et al, *Biochem. Pharmacol*. 1982;31:2257–2261) was also reported to activate GAD and increase GABA levels.

The compounds of the present invention have been found to activate GAD in vitro and have a dose dependent protective effect on-seizure in vivo.

Also, the compounds of the present invention have been found to bind a novel binding site which was identified to bind tritiated gabapentin. Gabapentin has been found to be an effective treatment for the prevention of partial seizures in patients refractory to other anticonvulsant agents. Chadwick D, *Gabapentin*, pp. 211–222, In: *Recent Advances in Epilepsy*, Vol. 5, Pedley T A, Meldrum B S, (eds.) Churchill Livingstone, N.Y. (1991). The novel binding site labeled by tritiated gabapentin was described in membrane fractions from rat brain tissue and in autoradiographic studies in rat brain sections, Hill D, Ibid. This binding site has been used to evaluate the compounds of the present invention.

The novel compounds of the present invention are set forth below as Formula I. It should be noted that the compound of Formula I wherein $R_1$ is methyl and each of $R_2$ and $R_3$ is hydrogen is taught in Japan Patent Number 49-40460.

SUMMARY OF THE INVENTION

In accordance with the present invention, there is provided compounds of the Formula I

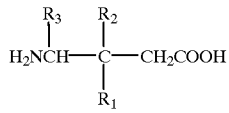

wherein $R_1$ is a straight or branched alkyl of from 1 to 6 carbons, phenyl or cycloalkyl having from 3 to 6 carbon atoms; $R_2$ is hydrogen or methyl; and $R_3$ is hydrogen, methyl, or carboxyl; with the proviso that when each of the $R_2$ and R3 is hydrogen, $R_1$ is other than methyl. Pharmaceutically acceptable salts of the compounds of Formula I are also included within the scope of the present invention. Also included within the scope of the present invention are the individual enantiomeric isomers of the compounds of the Formula I.

The present invention also provides pharmaceutical compositions of the compounds of Formula I.

Also provided as a part of the present invention is a novel method of treating seizure disorders in a patient by administering to said patient an anticonvulsant effective amount of a compound of the following Formula II

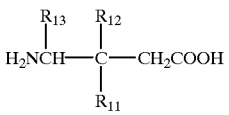

wherein $R_{11}$ is a straight or branched alkyl of from 1 to 6 carbon atoms, phenyl, or cycloalkyl having from 3 to 6 carbon atoms; $R_{12}$ is hydrogen or methyl; and $R_{13}$ is hydrogen, methyl, or carboxyl; or an individual enantiomeric isomer thereof; or a pharmaceutically acceptable salt thereof.

Also, the present invention provides a method for increasing brain neuronal GABA and provides pharmaceutical compositions of the compounds of Formula II.

The present invention provides novel processes for the synthesis of chiral Formula I compounds.

DETAILED DESCRIPTION OF THE INVENTION

In accordance with the present invention, there is provided a series of 3-alkyl-4-aminobutyric acid or 3-alkyl glutamic acid analogs which are useful as anticonvulsants. Illustrative of the alkyl moieties as represented by $R_1$ and $R_{11}$ in Formulas I and II are methyl, ethyl, propyl, isopropyl, n-butyl, isobutyl, sec-butyl, tert-butyl, isopentyl, and neopentyl as well as other alkyl groups. The cycloalkyl groups represented by $R_1$ and $R_{11}$ in Formulas I and II are exemplified by cyclopropyl, cyclobutyl, cyclopentyl, and cyclohexyl. The analogs are further shown herein to prevent seizure while not causing the side effect of ataxia, such a side effect being found in several anti-seizure pharmaceuticals.

The more preferred compounds of the present invention are of Formula I above wherein $R_3$ is hydrogen, $R_2$ is hydrogen, and $R_1$ isobutyl.

That is, the preferred compound is 4-amino-3-(2-methylpropyl)butanoic acid. It has been found that this compound is unexpectedly more potent than the other analogs synthesized in accordance herewith and tested in vivo. What is further surprising, as the following data shows, is that this preferred compound is the least effective one of the analogs tested in activating GAD in vitro. Accordingly, it was very unexpected that this preferred compound had such a high potency when tested in vivo.

The most preferred compounds of the present invention are the (S)-(+)- and the (R)(−)-4-amino-3-(2-methylpropyl) butanoic acid with the (S)-(+)-enantiomer being most preferred. The (S)-(+)-enantiomer was found to be the most potent compound within the scope of the present invention for displacement of tritiated gabapentin, and both the (S)-(+)- and the (R)-(−)-enantiomers showed pronounced stereoselectivity for both displacement of tritiated gabapentin and for anticonvulsant activity in vivo.

The compounds made in accordance with the present invention may form pharmaceutically acceptable salts with both organic and inorganic acids or bases. For example, the acid addition salts of the basic compounds are prepared either by dissolving the free base in aqueous or aqueous alcohol solution or other suitable solvents containing the appropriate acid and isolating the salt by evaporating the solution. Examples of pharmaceutically acceptable salts are hydrochlorides, hydrobromide, hydrosulfates, etc, as well as sodium, potassium, and magnesium, etc, salts.

The method for the formation of the 3-alkyl-4-aminobutanoic acids starting from 2-alkanoic esters is prepared from commercially available aldehydes and monomethyl malonate by the Knoevenagel reaction, (Kim YC, et al, J. Med. Chem. 1965:8509) with the exception of ethyl 4,4-dimethyl-2-pentenoate.

More specifically, the following is a procedure which can be generally applied to the preparation of all the 3-alkylglutamic acids. Ten grams of a 3-alkyl-5,5-dicarbethoxy-2-pyrrolidinone was refluxed in 150 mL of 49% fuming HBr for 4 hours. After this time, the contents were placed in an evaporator and the volatile constituents were removed in vacuo with the aid of a hot-water bath. The gummy residue was dissolved in 25 mL of distilled water and the water was removed with the aid of the evaporator. This. process was repeated once more. The residue was dissolved in 20 mL of water, and the pH of the solution was adjusted to 3.2 with concentrated NH3 solution. At this point the chain length of the individual 3-alkylglutamic acids altered the solubility so that those whose side chains were larger precipitated with the ease from solution. Precipitation of the alkylglutamic acids with smaller substituents (methyl, ethyl, and propyl) could be encouraged by cooling on an ice bath or by diluting the aqueous solution with 100 mL of absolute ethanol. Precipitation from the water-alcohol mixture is complete in 48 hours. Care must be taken to add the ethanol slowly to prevent the precipitation of an amorphous solid which is not characteristic of the desired 3-alkylglutamic acids. Samples of the amino acids were purified for analysis by recrystallizing from a water-ethanol mixture. All melted with decomposition. Melting points of the decomposed 3-alkylglutamic acids corresponded with those of their pyroglutamic acids.

Ethyl 4,4-dimethyl-2-pentenoate was prepared from 2,2-dimethylpropanol and ethyl lithioacetate, followed by dehydration of the β-hydroxy ester with phosphoryl chloride and pyridine.

The Michael addition of nitromethane to alpha, β-unsaturated compounds mediated by 1,1,3,3-tetramethylguanidine or 1,8-diazabicyclo-[5.4.0]undec-7-ene(DBU) afforded 4-nitroesters in good yields. More specifically, a mixture of nitromethane (5 mol), α,β-unsaturated ester (1 mol), and tetramethyl-guanidine (0.2 mol) was stirred at room temperature for 2 to 4 days. (In case of methyl acrylate, the ester has to be added at a temperature below 300.) The progress of the reaction was followed by IR (disappearance of the C=C band) and G.L.C. analysis. The reaction mixture was washed with dilute hydrochloric acid and extracted with ether. The organic extract was dried, the solvent removed at reduced pressure, and the 20 residue distilled at a pressure of 2 torr. Although the aliphatic nitro compounds are usually reduced by either high pressure catalytic hydrogenation by metal-catalyzed transfer hydrogenation, or by newly introduced hydrogenolysis methods with ammonium formate or sodium borohydride and palladium as catalysts, applicants have found that 4-nitrocarboxylic esters can be reduced almost quantitatively to the corresponding 4-aminocarboxylic esters by hydrogenation using 10% palladium on carbon as catalysts in acetic acid at room temperature and atmospheric pressure. The amino esters produced were subjected to acid hydrolysis to afford the subject inventive compounds in good yields. This procedure provides access to a variety of 3-alkyl-4-aminobutanoic acids as listed in Tables 1 and 2 as examples and thus is advantageous in comparison to methods previously used.

Examples of more specific methods of making compounds in accordance with the present invention are as follows, optionally utilizing the methods described in detail above. When the starting material is not commercially available, the synthetic sequence may be initiated with the corresponding alcohol, which is oxidized to the aldehyde by the method of Corey EJ, et al, *Tetrahedron Lett.* 1975:2647–2650.

The chiral compounds of Formulas I and II are prepared as set forth in the schematic in Chart I hereof. Although the schematic in Chart I depicts the chiral synthesis of specific compound (S)-(+)-4-amino-3-(2-methylpropyl)butanoic acid, one skilled in the art can readily see that the method of synthesis can be applied to any diastereomeric compound of Formulas I and II.

In Chart I Ph is phenyl, Bn is benzyl, THF is tetrahydrofuran, LDA is lithium diisopropylamide, $BH_3 \cdot SMe_2$ is borane dimethyl sulfide complex, TsCl is tosyl chloride, and DMSO is dimethylsulfoxide.

The detailed synthetic procedure is set forth hereinbelow in Example 1. The key introductory literature for this methodology was discussed in Evans' paper, *J. Am. Chem. Soc.* 1982;104:1737–9. The metal enolate can be formed with a lithium or sodium amide base, and subsequently alkylated to give an a substituted carboxylic acid derivative. This methodology was valuable for the enantioselective synthesis of these α-substituted carboxylic acid derivatives. In this seminal paper, Evans described the preparation of propionic acid derivatives with a series of simple alkylating agents. By varying the stereochemistry of the chiral synthon (the oxazolidinone), he was able to get high stereoselectivity.

Evans has used this chiral auxiliary in other synthetic studies, but none has been related to 4-amino-3-(2-methylpropyl)butanoic acid which contains a β-substituted-γ-amino acid. The methodology as presented by Evans teaches toward a-substitution, and away from γ-substitution, and has not been used in the preparation of this type of unusual amino acid. N-acyloxazolidinones have been used to form chlorotitanium enolates that have been reacted with Michael adducts such as acrylonitrile, *J. Org. Chem.* 1991;56:5750–2. They have been used in the synthesis of the rutamycin family of antibiotics, *J. Org. Chem.* 1990;55:6260–8 and in stereoselective aldol condensations, *Org. Synth.* 1990;68:83–91. Chiral α-amino acids were prepared via the oxazolidinone approach. In this sequence, a dibutylboron enolate was brominated and displaced with azide, *Tetrahedron Lett.* 1987;28:1123–6. Other syntheses of β-hydroxy-α-amino acids were also reported via this chiral auxiliary through aldol condensation (*Tetrahedron Lett.* 1987;28:39–42; *J. Am. Chem. Soc.* 1987;10:7151–7). α,β-Unsaturated N-acyloxazolidinones have also been used to induce chirality in the Diels-Alder reaction, (*J. Am. Chem. Soc.* 1988;110:1238–56. In none of these examples, or others found in the literature, is this methodology used to prepare (β-substituted carboxylic acids or 3-substituted GABA analogs.

In another embodiment, the chiral compounds of Formulas I and II can be prepared in a manner which is similar to the synthesis depicted in Chart I. In this embodiment, however, step 8 in Chart I is replaced by an alternate two step procedure which is set forth hereinbelow in Example 2 (sodium hydroxide is preferred, however, other solvents known to those of skill in the art which can hydrolyze the azide (8) to intermediate azide (8a) can be employed). Instead of reducing the azide (8) to the amino acid (9) in Chart I, the alternate procedure hydrolyzes the azide (8) to give an intermediate azide (8a) which is subsequently reduced (see Chart Ia).

There are two major advantages to hydrolyzing azide (8) to give the intermediate azide (8a) prior to reduction. The first advantage is that intermediate azide (8a) may be purified by extraction into aqueous base. After the aqueous extract is acidified, intermediate azide (8a) may be extracted into the organic phase and isolated. This allows for a purification of intermediate azide (8a) which does not involve chromatography. The purification of azide (8) requires chromatography which is very expensive and often impractical on a large scale.

The second advantage is that intermediate azide (8a) may be reduced to amino acid (9) without added acid. Reduction of azide (8) requires addition of acid, e.g., hydrochloric acid in order to obtain amino acid (9). Unfortunately, lactamization of amino acid (9) is promoted by the presence of acid. Intermediate azide (8a) may be reduced under near neutral conditions to give amino acid (9), thus minimizing the problem of lactam formation.

In another preferred embodiment, the chiral compounds of Formulas I and II can be prepared as set forth in the Schematic in Chart II hereof. Although the schematic in Chart II depicts the chiral synthesis of specific compound (S)-(+)-4-amino-3-(2-methyl-propyl)butanoic acid, one skilled in the art can readily see that the method of synthesis can be applied to any diastereomeric compound of Formulas I and II.

In Chart II Ph is phenyl, and Ts is tosyl.

The detailed synthetic procedure is set forth hereinbelow in Example 3. This procedure is similar to the synthesis route depicted in Chart I, however, the procedure of Chart II replaces the benzyl ester in the synthesis route of Chart I with a t-butyl ester. The desired amino acid (9) and (109) is the same end product in both Charts I and II, respectively.

There are several advantages to using the t-butyl ester rather than the benzyl ester in the synthesis of amino acid (9) or (109). A first advantage relates to the hydrolysis of the chiral auxiliary in step 4 of Chart 1. During the hydrolysis of the chiral auxiliary in this reaction some hydrolysis of the benzyl ester often occurs. Hydrolysis of the t-butyl ester in Chart II has not been experienced.

Another advantage relates to the use of alcohol (106) in Chart II over the use of alcohol (6) in Chart I. A problem with the benzyl ester-alcohol is the tendency of the benzyl ester-alcohol to undergo lactonization as shown below. Although lactonization of the benzyl ester can be avoided under some conditions, the t-butyl ester-alcohol is far less prone to lactonization.

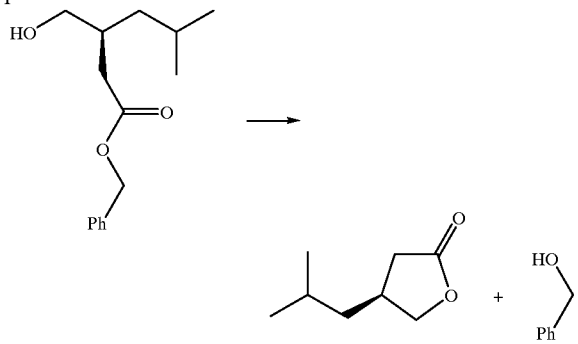

Still another advantage, which was previously discussed with regard to the synthetic procedure depicted by Chart Ia, is that the t-butyl synthetic route minimizes the problem of lactam formation of the amino acid end product (109). Instead of reducing azide (108) to amino acid (109) which requires the addition of acid that causes lactamization of amino acid (109), azide (108) is first hydrolyzed to intermediate azide (108a). Intermediate azide (108a) may be reduced under neutral conditions to give amino acid (109), thus minimizing the problem of lactam formation.

It should also be mentioned that several novel intermediates are produced by the processes discussed herein. Some of these intermediates which are depicted in Charts I, Ia, and II include in the racemate or R or S enantiomer form:

4-methyl-5-phenyl-2-oxazolidinone, 4-methyl-(2-methylpropyl)-2-dioxo-5-phenyl-3-oxazolidine butanoic acid, phenylmethyl ester, 4-methyl-pentanoyl chloride, 4-methyl-3-(4-methyl-1-oxopentyl)-5-phenyl-2-oxazolidinone, 2-(2-methylpropyl)-butanedioic acid, 4-(phenylmethyl) ester, 3-(azidomethyl)-5-methyl-hexanoic acid, phenylmethyl ester, 3-(hydroxymethyl)-5-methyl-hexanoic acid, phenylmethyl ester, 5-methyl-3-[[[(4-methylphenyl)sulfonyl]oxyl-methyl]-hexanoic acid, phenylmethyl ester, 3-(azidomethyl)-5-methyl-hexanoic acid, 2-(2-methylpropyl)-1,4-butanedioic acid, 4-(1,1-dimethylethyl) ester, 3-(azidomethyl) -5-methyl-, 1,1-dimethylethyl ester, 3-(hydroxymethyl)-5-methyl-hexanoic acid, 1,1-dimethyl ester, 5-methyl-3-[[[(4-methyl(phenyl)sulfonyl]oxy]-methyl-hexanoic acid, 1,1-dimethylethyl ester, or 4-methyl-(2-methylpropyl)-2-dioxo-5-phenyl-3-oxazolidinebutanoic acid, 1,1-dimethylethyl ester.

The compounds made by the aforementioned synthetic methods can be used as pharmaceutical compositions as an antidepressant, anxiolytic, antipsychotic, antiseizure, antidyskinesic, or antisymptomatic for Huntington's or Parkinson's diseases when an effective amount of a compound of the aforementioned formula together with a pharmaceutically acceptable carrier is used. That is, the present invention provides a pharmaceutical composition for the suppression of seizures resulting from epilepsy, the treatment of cerebral ischemia, Parkinson's disease, Huntington's disease and spasticity and also possibly for antidepressant, anxiolytic, and antipsychotic effects. These latter uses are expected due to functional similarities to other known compounds having these pharmacological activities. The pharmaceutical can be used in a method for treating such disorders in mammals, including human, suffering therefrom by administering to such mammals an effective amount of the compound as described in Formulas I and II above in unit dosage form.

The pharmaceutical compound made in accordance with the present invention can be prepared and administered in a wide variety of dosage forms. For example, these pharmaceutical compositions can be made in inert, pharmaceutically acceptable carriers which are either solid or liquid. Solid form preparation include powders, tablets, dispersible granules, capsules, cachets, and suppositories. Other solid and liquid form preparations could be made in accordance with known methods of the art. The quantity of active compound in a unit dose of preparation may be varied or adjusted from 1 mg to about 300 mg/kg (milligram per kilogram) daily, based on an average 70 kg patient. A daily dose range of about 1 mg to about 50 mg/kg is preferred. The dosages, however, may be varied depending upon the requirement with a patient, the severity of the condition being treated, and the compound being employed. Determination of the proper dosage for particular situations is within the skill of the art.

Illustrative examples of compounds made in accordance with the present invention were tested to demonstrate the ability of the compounds to activate GAD in vitro and to prevent seizure in vivo without the side effect of ataxia.

In Vitro GAD Activation

Assays were carried out in 10 mL vials sealed with serum caps through which a center well (Kontes Catalog No. 882320-000) was inserted. The center well was charged with 200 μL of freshly prepared 8% KOH solution. Various concentrations of L-glutamic acid (0.5, 0.25, 0.166, 0.125, 0.10 mM) containing [$^{14}$C]L-glutamate (10 μCi/mmol) in 50 mM potassium phosphate buffer, pH 7.2 were shaken at 37° C. in separate vials with purified L-glutamic acid decarboxylase (18.75 μg; spec. act 10.85 μmol/min mg) in a total volume of 2.00 mL. After being shaken for 60 minutes, the enzyme reactions were quenched by the addition of 200 μL of 6 M sulfuric acid to the contents of each of the vials. The vials were shaken for an additional 60 minutes at 37° C. The center wells were removed and placed in scintillation vials with 10 mL of scintillation fluid for radioactivity determination. The same assays were repeated except in the presence of various concentrations of the activators (2.5, 1.0, 0.5, 0.25, 0.1, 0.05 mM). The Vmax values were determined from plots of 1/cpm versus 1/[glutamate] at various concentrations of activators. The data were expressed as the ratio of the Vmax in the presence of the activators to the Vmax in the absence of the activators times 100%.

The results of the experiment are shown in Table 1. The tests show that there was significant activation by the various compounds tested to differing degrees. The known activator sodium valproate and gabapentin were tested.

In vivo tests were performed to demonstrate the seizure preventing capabilities of the novel compounds. Threshold maximum electroshock is an animal model test for generalized seizures that is similar to that of Piredda S G, et al, Pharmacol. and Exptl. Therap. 1985;232(3):741–45. The methods for this test are described as follows.

Male CF-1 mice (22–30 g) were allowed free access to food and water prior to testing. For screening, groups of five mice were given a compound intravenously at doses of 30, 100, and 300 mg/kg and tested at 0.5, 2.0, and 4.0 hours after dosing. Drugs were either dissolved in 0.9% saline or suspended in 0.2% methylcellulose. Animals were shocked with corneal electrodes (see below) and observed for tonic hindlimb extensor seizures. Absence of hindlimb extension was taken as an anticonvulsant effect.

The electroshock apparatus delivered a 60 Hz sine wave with a current amplitude of 14 mA (peak-to-peak) for 0.2 seconds. The current strength of 14 mA used in this procedure produced tonic extensor seizures in approximately 95% of untreated mice, but was only slightly above threshold for tonic extension.

Summaries of the numbers of animals protected from seizures when tested 120 minutes after administration of each compound set forth in the left-hand column are given in Table 2 for varying dose levels set forth in the second column of the table.

Due to the interesting phenomena related to the (R,S)-i-butyl GABA (the compound having significantly higher potency and effectiveness without causing ataxia), threshold maximal electroshock tests where conducted varying the time of testing from 1 hour to 8 hours, the dose being 10 mg/kg in mice, injected intravenously. Table 3 shows the results of these tests indicating a maximum protection after 2 hours of testing.

In view of the above results, a dose response curve was made for the two hour testing time period in mice, the drug being given intravenously at 10 mg/kg. The results of this test is shown in Table 4 with a calculated ED50 equaling 2.07 mg/kg.

A third pharmacological test was performed as described in Krall RL, et al, *Epilepsia*. 1978;19:409. In this procedure, drugs were tested for attenuation of threshold clonic seizures in mice caused by subcutaneous administration of pentylenetetrazol (85 mg/kg) which is a generally accepted model for absence type seizures. Results from the third test for the compound when administered either intravenously or orally is shown in Table 5. The test was conducted at three dose levels, showing effective protection at 30 mg/kg and 100 mg/kg with no ataxia.

The above is a significant finding because the compound having the least ability to activate GAD in vitro surprisingly had an approximately 10-fold increase in potency over the other compounds tested. Even more unexpected is the absence of ataxic side effect coupled to this increase in potency.

TABLE 1

Activation of GAD by GABA analogs at various concentrations expressed in %

$$H_3N^+CH_2\underset{R_1}{\overset{R_2}{C}}CH_2COO^-$$

| $R_1, R_2$ | 2.5 mM | 1.0 mM | 0.5 mM | 0.25 mM | 0.1 mM | 0.05 mM |
|---|---|---|---|---|---|---|
| (R,S)—CH$_3$,H | 239 | 168 | 142 | 128 | 118 | 107 |
| (R)—CH$_3$H | 327 | 202 | 185 | 135 | 128 | 109 |
| (S)—CH$_3$H | 170 | 118 | — | 103 | — | — |
| CH$_3$, CH$_3$ | 174 | 125 | — | 109 | — | — |
| (R,S)—C$_2$H$_5$,H | 172 | 128 | — | 108 | — | — |
| (R,S)-n-C$_3$H$_7$,H | 156 | 112 | — | 105 | — | — |
| (R,S)-i-C$_3$H$_7$,H | 140 | 108 | — | 104 | — | — |
| (R,S)-n-C$_4$H$_9$,H | 178 | 117 | — | 105 | — | — |
| (R,S)-i-C$_4$H$_9$,H | 143 | 113 | — | 109 | — | — |

TABLE 1-continued

| | | | | | | |
|---|---|---|---|---|---|---|
| (R,S)-s-C$_4$H$_9$,H | 169 | 119 | — | 105 | — | — |
| 4R,S)-t-C$_4$H$_9$,H | 295 | 174 | 147 | 121 | 117 | 108 |
| (R,S)-neo-C$_5$H$_{11}$,H | 279 | 181 | — | 130 | — | — |
| (R,S)-i-C$_5$H$_{11}$,H | 142 | 118 | — | 109 | — | — |
| (R,S)-C$_6$H$_{11}$,H | 125 | 100 | — | 100 | — | — |
| (R,S)-C$_6$H$_5$,H | 218 | 129 | — | 110 | — | — |

$$H_3N\overset{CH_3}{\underset{R}{CHCHCH_2COO^-}}$$

| R | 2.5 mM | 1.0 mM | 0.5 mM | 0.25 mM | 0.1 mM | 0.05 mM |
|---|---|---|---|---|---|---|
| H(R,S) | 140 | 111 | — | 104 | — | — |
| H(R) | 173 | 125 | — | 108 | — | — |
| H(S) | 100 | 100 | — | 100 | — | — |
| CH$_3$ | 143 | 121 | — | 109 | — | — |
| C$_6$H$_5$ | 207 | 151 | — | 112 | — | — |
| Sodium Valproate | 207 | 138 | 124 | 119 | 115 | 105 |
| GABAPENTIN | 178 | 145 | — | 105 | — | — |

Activation of GAD by glutamate analogs expressed in %

$$H_3N^+\text{—}CH\overset{COO^-}{\underset{R}{\text{—}CH\text{—}}}CH_2\text{—}COOH$$

| R | 2.5 mM | 1.0 mM | 0.25 mM |
|---|---|---|---|
| CH$_3$ | 212 | 144 | 113 |
| C$_2$H$_5$ | 170 | 128 | 113 |
| n-C$_3$H$_7$ | 153 | 125 | 108 |
| i-C$_3$H$_7$ | 144 | 114 | 105 |
| n-C$_4$H$_9$ | 133 | 117 | 105 |
| i-C$_4$H$_9$ | 129 | 112 | 106 |
| C$_6$H$_5$ | 172 | 135 | 112 |
| Sodium Valproate | 207 | 138 | 119 |

TABLE 2

Prevention of tonic extensor seizures in mice following intravenous administration of 3-substituted GABA derivatives

| R | Dose (mg/kg) | Time After Dose (min) | Effect # Protected/ # Tested | Ataxia # Ataxia/ # Tested |
|---|---|---|---|---|
| (R,S) —CH$_3$ | 10 | 120 | 0/5 | 0/5 |
| | 30 | 120 | 4/5 | 0/5 |
| | 100 | 120 | 3/5 | 0/5 |
| CH$_3$ | 1 | 120 | 1/10 | 0/10 |
| | 3 | 120 | 2/10 | 0/10 |
| | 10 | 120 | 4/10 | 0/10 |
| | 30 | 120 | 3/10 | 0/10 |
| | 100 | 120 | 3/10 (5/10) | 1/10 |
| CH$_3$ | 10 | 120 | 1/10 | 1/10 |
| | 30 | 120 | 2/10 | 0/10 |
| | 100 | 120 | 5/10 | 0/10 |
| t-C$_4$H$_9$ | 10 | 120 | 2/10 | 0/10 |
| | 30 | 120 | 2/10 | 0/10 |
| | 100 | 120 | 5/10 | 0/10 |
| C$_2$H$_5$ | 3 | 120 | 1/5 | 0/5 |
| | 10 | 120 | 1/5 | 0/5 |
| | 30 | 120 | 2/5 | 0/5 |
| | 100 | 120 | 5/5 | 0/5 |
| (CH$_3$)$_2$ | 30 | 120 | 4/5 | 0/5 |
| | 100 | 120 | 4/5 | 0/5 |

TABLE 2-continued

Prevention of tonic extensor seizures in mice following intravenous administration of 3-substituted GABA derivatives

| R | Dose (mg/kg) | Time After Dose (min) | Effect # Protected/ # Tested | Ataxia # Ataxia/ # Tested |
|---|---|---|---|---|
| n-C$_4$H$_9$ | 10 | 120 | 1/10 | 0/10 |
|  | 30 | 120 | 3/10 | 0/10 |
|  | 100 | 120 | 4/10 | 0/10 |
| s-C$_4$H$_9$ | 3 | 120 | 2/10 | 0/10 |
|  | 10 | 120 | 3/10 | 0/10 |
|  | 30 | 120 | 2/10 | 0/10 |
| i-C$_4$H$_9$ | 0.3 | 120 | 1/10 | 0/10 |
|  | 0.8 | 120 | 3/10 | 0/10 |
|  | 2.0 | 120 | 5/10 | 0/10 |
|  | 5.5 | 120 | 7/10 | 0/10 |
|  | 14.4 | 120 | 9/10 | 0/10 |
| n-C$_3$H$_7$ | 3 | 120 | 2/10 | 0/10 |
|  | 10 | 120 | 2/10 | 3/10 |
|  | 100 | 120 | 3/10 | 0/10 |
| i-C$_3$H$_7$ | 10 | 120 | 5/10 | 1/10 |
|  | 30 | 120 | 5/10 | 0/10 |
|  | 100 | 120 | 6/10 | 0/10 |
| C$_6$H$_5$ | 100 | 120 | 0/10 | 0/10 |
| neo-C$_5$H$_{11}$ | 10 | 120 | 2/10 | 0/10 |
|  | 30 | 120 | 4/10 | 0/10 |
|  | 100 | 120 | 4/10 | 0/10 |

High-intensity corneal electroshock consisted of 50 mA, base-to-peak sinusoidal current for 0.2 seconds.
All other data was from low-intensity electroshock, 17 mA base-to-peak sinusoidal current for 0.2 seconds.

TABLE 3

Threshold maximal electroshock with isobutyl GABA

| Time of Testing | # Protected |
|---|---|
| 1 hr. | 2/10 |
| 2 hr. | 8/10 |
| 4 hr. | 4/10 |
| 8 hr. | 2/10 |

TABLE 4

Threshold maximal electroshock with isobutyl GABA

| Dose m/k | # Protected |
|---|---|
| 0.3 | 1/10 |
| 0.8 | 3/10 |
| 2.0 | 5/10 |
| 5.5 | 7/10 |
| 14.4 | 9/10 |

TABLE 5

Maximal electroshock data

| R | Dose (mg/kg) | Time After Dose (min) | Effect # Protected/ # Tested | Ataxia # Ataxia/ # Tested |
|---|---|---|---|---|
| i-C$_4$H$_9$ | 10 | 120 | 1/5 | 0/5 |
| i-C$_4$H$_9$ | 30 | 120 | 4/5 | 0/5 |
| i-C$_4$H$_9$ | 100 | 120 | 4/5 | 0/5 |

As noted hereinabove, the S-(+) enantiomer of 4-amino-3-(2-methylpropyl)butanoic acid (3-isobutyl GABA or IBG) which is structurally related to the known anticonvulsant, gabapentin, potently displaces tritiated gabapentin from a novel high-affinity site in rat brain membrane fractions. Also the S-(+)enantiomer of 3-isobutyl GABA is responsible for virtually all blockade of maximal electroshock seizures in mice and rats. The R(–) enantiomer of 3-isobutyl GABA is much less effective in the blockade of maximal electroshock seizures and in displacement of tritiated gabapentin from the novel high-affinity binding site. Table 6 below sets forth data comparing gabapentin, racemic 3-isobutyl GABA ((±)-IBG), S-(+)-3-isobutyl GABA ((S)-IBG) and R-(–)-3-isobutyl GABA ((R)-IBG) in these assays.

TABLE 6

| | 3-Isobutyl GABA (ED$_{50}$) | | | |
|---|---|---|---|---|
| Test System | Gabapentin | (±)-IBG | (S)-IBG | (R)-IBG |
| Gabapentin Receptor Binding (IC$_{50}$) | 0.14 µM | 0.10 µM | 0.044 µM | 0.86 µM |
| IV Mouse Low-Intensity Electroshock | 4.3 mg/Kg | 4.8 mg/Kg | 4.0 mg/Kg | >100 mg/Kg |
| IV Mouse Maximal Electroshock | 75 mg/Kg | 10 mg/Kg | 18 mg/Kg | >100 mg/Kg |
| PO Mouse Maximal Electroshock | 200 mg/Kg | 47 mg/Kg | 12 mg/Kg | |
| IV Mouse Ataxia | >100 mg/Kg (IP) | >100 mg/Kg | >300 mg/Kg | >100 mg/Kg |

Time course of anticonvulsant activity (all compounds) peaks 2.0 hours after dose and mostly gone 8 hours after dose.

The data set forth in Table 6 was obtained as follows. For anticonvulsant testing, male CF-1 strain mice (20–25 g) and male Sprague-Dawley rats (75–115 g) were obtained from Charles River Laboratories and were maintained with free access to food and water before testing. Maximal electroshock was delivered with corneal electrodes by conventional methods (Krall, supra, 1975) except that low-intensity electroshock with mice consisted of 17 mA of current rather than the conventional 50 mA (zero to peak). Briefly, mice were given test substance and were tested for prevention of seizures by application of electrical current to the corneas by 2 metal electrodes covered with gauze and saturated with 0.9% sodium chloride. Electroshock stimulation was delivered by a constant-current device that produced 60 Hz sinusoidal electrical current for 0.2 seconds. For rats, maximal electroshock stimulation consisted of 120 mA of current. Ataxia in mice was assessed by the inverted screen procedure in which mice were individually placed on a 4.0-inch square of wire mesh that was subsequently inverted (Coughenour, supra, 1978). Any mouse that fell from the wire mesh during a 60 second test period was rated as ataxic. $ED_{50}$ values were determined by probit analysis of results with at least 5 dose groups of 10 mice or 8 rats each.

All drugs were freely soluble in aqueous media. For in vivo studies, drug solutions were made in 0.9% sodium chloride and given in a volume of 1 mL/100 g body weight. Intravenous administration was given by bolus injection into the retro-orbital sinus in mice. Oral administrations were by intragastric gavage.

For binding studies, partially purified synaptic plasma membranes were prepared from rat neocortex using sucrose density gradients. The cerebral cortex of 10 rats was dissected from the rest of the brain and homogenized in 10 volumes (weight/volume) of ice-cold 0.32 M sucrose in 5 mM tris-acetate (pH 7.4) using a glass homogenizer fitted with a teflon pestle (10–15 strokes at 200 rpm). The homogenate was centrifuged at 100 g for 10 minutes and the supernatant collected and kept on ice. The pellet (PI) was rehomogenized in 20 mL of tris-sucrose and the homogenate recentrifuged. The combined supernatants were centrifuged at 21,500 g for 20 minutes. The pellet (P2) was resuspended in 1.2 M tris-sucrose and 15 mL of this mixture was added to ultracentrifuge tubes. On to this, 10 mL of 0.9 M sucrose was layered followed by a final layer of 5 mM tris-acetate, pH 8.0. Tubes were centrifuged at 100,000 g for 90 minutes. The synaptic plasma membranes located at the 0.9/1.2 M sucrose interface were collected, resuspended in 50 mL of 5 mM tris-acetate, pH 7.4, and centrifuged at 48,000 g. The final pellet was resuspended in 50 mL of tris-acetate, pH 7.4, aliquoted, and then frozen until use.

The assay tissue (0.1 to 0.3 mg protein) was incubated with 20 mM $^3$H]-gabapentin in 10 mM HEPES buffer (pH 7.4 at 20° C., sodium free) in the presence of varying concentrations of test compound for 30 minutes at room temperature, before filtering onto GFB filters under vacuum. Filters were washed 3 times with 5 mL of ice cold 100 mM NaCl solution and dpm bound to filters was determined using liquid scintillation counting. Nonspecific binding was defined by that observed in the presence of 100 mM gabapentin.

In view of the above demonstrated activity of the compounds characterizing the present invention and in particular the 4-amino-3-(2-methylpropyl)butanoic acid (isobutyl GABA) the compounds made in accordance with the present invention are of value as pharmacological agents, particularly for the treatment of seizures in mammals, including humans.

EXAMPLE 1

(S)-(+)-4-amino-3-(2-methylpropyl)butanoic acid

The following "steps", refer to Chart I.
Step 1

To a solution of 4-methylvaleric acid (50.0 g, 0.43 mol) in 100 mL of anhydrous chloroform was added thionyl chloride (60 mL, 0.82 mol). The reaction mixture was refluxed for 2 hours and then cooled to room temperature. Excess chloroform and thionyl chloride was removed by distillation. The residue oil was then fractionally distilled to give 45.3 g (78%) of the acid chloride (2), bp=143–144° C.

Acid chloride (2) was also be prepared by an alternative method which eliminated use of chloroform which has waste disposal and operator exposure difficulties. The alternate method also minimized the formation of 4-methylvaleric anhydride.

To a solution of thionyl chloride (98.5 kg, 828 mol) and N,N-dimethylformamide (2 kg, 27 mol) was added 4-methylvaleric acid (74 kg, 637 mol) while maintaining a reaction temperature of 25–30° C. Hexanes (30 L) were added and the solution was maintained at 30–35° C. for 1 hour and 15 minutes. The solution was then heated to 70–75° C. for 1 hour and 10 minutes. The solution was subjected to atmospheric distillation until a solution temperature of 95° C. was reached. After cooling, hexanes (30 L) were added and the solution was subjected to atmospheric distillation until a solution temperature of 97° C. was reached. Distillation of the residual oil produced 79 kg (92%) of acid chloride (2), bp=–77° C., 60–65 mm Hg.
Step 2

To a solution of (4R,5S)-(+)-4-methyl-5-phenyl-2-oxazolidinone (5.27 g, 29.74 mmol) in 70 mL of anhydrous tetrahydrofuran at –78° C. under argon atmosphere was added a 1.6 M solution of n-butyllithium (19 mL, 30.40 mmol) in hexanes slowly. The mixture was allowed to stir at –78° C. for 15 minutes then the acid chloride (4.5 g, 33.43 mmol) was added to quench the reaction. The reaction was stirred at –78° C. for 10 minutes then 0° C. for 30 minutes. A saturated solution of sodium bicarbonate (50 mL) was added and the mixture was stirred at 0° C. for 30 minutes. The organic layer was collected and the aqueous layer was extracted with ethyl acetate (3×). The organic extracts were combined and dried with anhydrous magnesium sulfate. It was then filtered and concentrated to give a colorless oil. The oil was then chromatographed with 8% ethyl acetate in hexanes on silica gel to give 7.56 g (82%) of the acyloxazolidinone (3) as a white solid.

Anal. Calcd for $C_{16}H_{21}NO_3$: C, 69.79; H, 7.69; N, 5.09. Found: C, 69.56; H, 7.63; N, 5.06.

Acyloxazolidinone (3) was also prepared by an alternate method which was conducted at –5° C. to 0° C. rather than –78° C. which is difficult and expensive to achieve on a manufacturing scale. The alternate method also gave a crystalline solid from the reaction mixture rather than an oil which must be chromatographed.

To a solution of 4-methyl-5-phenyl-2-oxazolidinone (64 g, 0.36 mol) in anhydrous tetrahydrofuran (270 g) at –5° C. was added a 15% solution of n-butyllithium in hexane (160 g, 0.37 mol) over a temperature range of –5° C. to 0° C. Acid chloride (2) (48.6 g, 0.36 mol) was added at –10° C. to 0° C. The reaction was quenched with a solution of water (90 mL) and sodium bicarbonate (4 g). Ethyl acetate (200 g) was added and the layers were separated. The organic layer was extracted with water (2×50 mL) and the aqueous phases were back extracted with ethyl acetate (100 g). The organic extracts were combined and approximately 150 mL of solvent was removed by distillation. Atmospheric distillation was continued and heptane (2×200 g) was added until a vapor temperature of 95° C. was reached. The solution was cooled to 5° C. The product was collected by filtration, washed with cold heptane, and dried to give 79 g (80%) of acyloxazolidinone (3).
Step 3

To a solution of diisopropylamine (4.8 mL, 34.25 mmol) in 30 mL of anhydrous tetrahydrofuran at 0° C. under argon atmosphere was added a 1.6 M solution of n-butyllithium (21 mL, 33.60 mmol) in hexanes slowly. The solution was stirred at 0° C. for 30 minutes then cooled to –78° C. A solution of the acyloxazolidinone (3) (7.56 g, 27.46 mmol) in 30 mL of anhydrous tetrahydrofuran was added and the pale yellow solution was stirred at −78° C. for 30 minutes. Benzyl α-bromoacetate was added and the resulting solution was stirred at −25° C. for 2 hours. The reaction mixture was quenched with a half-saturated ammonium chloride solution and extracted by ethyl acetate (2×). The combined organic layers were dried with anhydrous magnesium sulfate and then filtered and concentrated to give a colorless oil. The oil was then chromatographed with 8% ethyl acetate in hexanes on silica gel to give 6.16 g (53%) of the acyloxazolidinone (4) as a white solid.

Anal. Calcd for $C_{25}H_{29}NO_5$: C, 70.90; H, 6.90; N, 3.31. Found: C, 70.47; H, 6.87; N, 3.45.

Acyloxazolidinone (4) was also prepared by an alternate method that was advantageous in that the reaction was conducted a higher temperature (−35° C. to −25° C. rather than −78° C.) and an expensive and difficult chromatographic separation was avoided.

Acyloxazolidinone (3) (85 kg, 308 mol) was dissolved in anhydrous tetrahydrofuan (201 kg) and cooled to −30° C. Lithium diisopropyl amine (340 mol) in methyl-t-butyl ether/hexane was added while maintaining a reaction temperature of 35° C. to −25° C. Benzyl bromoacetate (85 kg, 371 mol) was then added while maintaining a reaction temperature of −35° C. to −25° C. Water (60 kg) and methyl-t-butyl ether (93 kg) were added and the mixture was allowed to warm to 18° C. The layers were separated and the organic layer was extracted with a solution of water (40 L) and sodium chloride (7 kg). The layers were separated and the organic layer was concentrated to 200 liters by distillation. Isopropyl alcohol (200 L) was added and the solution was again concentrated to 200 liters by distillation. Isopropyl alcohol (425 L) and water (160 L) were added and the mixture was heated to 50° C. The solution was cooled to 18° C. The product was collected by filtration, washed with isopropyl alcohol/water and dried under reduced pressure to give 58.7 kg (49% yield) of acyloxazolidinone (4) as a solid.

Step 4

To a pre-cooled (0° C.) solution of the 0 acyloxazolidinone (4) (24.3 g, 57.38 mmol) in 600 mL of tetrahydrofuran was added a solution of 30% hydrogen peroxide (23.7 mL) in 320 mL of 0.2 M lithium hydroxide solution via a dropping funnel in 20 minutes. The reaction mixture was allowed to stir at 0° C. for 4 hours. A solution of sodium meta-bisulphite (62.2 g, 0.33 mol) in 320 mL of water was then added slowly to quench the reaction. The mixture was stirred at 0° C. for 20 minutes. Excess tetrahydrofuran was removed on a rotavap. The aqueous residue was extracted with ethyl acetate (3×350 mL). The combined organic extracts were dried with anhydrous magnesium sulfate and then filtered. The oily residue after concentration was chromatographed by 40% ethyl acetate in hexane on silica gel to give 13.34 g (88%) of the acid (5) as a clear oil. The column was then eluted with 50% ethyl acetate in hexane to give the oxazolidinone chiral auxiliary.

$^1$H NMR (300 MHz, $CDCl_3$) of acid (5): δ 9.80 (br s, 1H), 7.36 (m, 5H), 5.14 (narrow ABq, 2H, $J_{AB}$=11.4 Hz), 2.80 (m, 1H), 2.63 (ABX, 2H, $J_{AB}$=16.75 Hz, $J_{AB}$=9.13 Hz, $J_{BX}$=5.16 Hz, $U_{AB}$=73.20 Hz), 1.66 (m, 2H), 1.33 (m, 1H), 0.93 (d, 3H, J=7.32 Hz), 0.91 (d, 3H, J=6.45 Hz).

In an alternate method, after concentration of the reaction to an oily residue, hexane or heptane may be added in order to precipitate the oxazolidinone chiral auxiliary. Filtration then yields the chiral auxiliary in 80% recovery. The hexane or heptane filtrate containing acid (5) is then extracted with either an ethanol water solution or with warm water to remove any remaining chiral auxiliary. This alternative method avoids a costly and difficult chromatographic separation of the chiral auxiliary from the acid (5).

Step 5

To a solution of the acid (5) (13.34 g, 50.47 mmol) in 460 mL anhydrous tetrahydrofuran at 0° C. under argon was added borane dimethyl sulfide complex (10 M, 11.2 mL, 112.0 mmol) slowly. The reaction mixture was stirred at 0° C. for 30 minutes then room temperature for 4 hours. The reaction was cooled to 0° C. and 250 mL of methanol was added slowly. The mixture was stirred at 0° C. for 30 minutes and excess. solvent was removed under vacuum. The resulting oil was chromatographed by 15% ethyl acetate in hexanes on silica gel to give 10.59 g (84%) of the alcohol (6) as a colorless oil.

$^1$H NMR (300 MHz, $CDCl_3$): δ7.37 (m, 5H), 5.14 (s, 2H), 3.57 (ABX, 2H, $J_{AB}$=10.99 Hz, $J_{AX}$=4.34 Hz, $J_{BX}$=6.85 Hz, υAB=51.71 Hz), 2.42 (ABX, 2H, $J_{AB}$=15.26 Hz, $J_{AX}$=7.60 Hz, $J_{BX}$=5.56 Hz, $υ_{AB}$=18.81 Hz), 2.15 (m, 1H), 1.87 (br s, 1H), 1.63 (m, 1H), 0.93 (m, 2H), 0.88 (d, 3H, J=6.15 Hz), 0.87 (d, 3H, J=6.45 Hz).

Step 6

To a solution of the alcohol (6) (10.22 g, 40.82 mmol) in 50 mL of anhydrous pyridine at 0° C. was added tosyl chloride (8.60 g, 45.11 mmol). The reaction mixture was stirred at 0° C. for 15 minutes then stood overnight in a refrigerator at 4° C. The reaction mixture was diluted with 160 mL of ethyl acetate and 100 mL of water. The mixture was cooled to 0° C. in an ice-water bath and then concentrated hydrochloric acid was added slowly to neutralize excess pyridine (until pH 2). The organic layer was collected and the aqueous layer was extracted with ethyl acetate (3×100 mL). The combined organics were dried with anhydrous magnesium sulfate and then filtered. The resulting pale yellow oil after concentration was chromatographed by 10% ethyl acetate in hexanes on silica gel to give 14.44 g (87%) of the tosylate (7) as a colorless oil.

$^1$H NMR (300 MHz, $CDCl_3$): δ 7.77 (d, 2H, J=8.27 Hz), 7.34 (m, 7H), 5.07 (s, 2H), 4.00 (ABX, 2H, $J_{AB}$=9.77 Hz, $J_{AX}$=4.07 Hz, $J_{BX}$=5.69 Hz, $υ_{AB}$=27.58 Hz), 2.44 (s, 1H), 2.44–2.20 (m, 3H), 1.46 (m, 1H), 1.28–1.02 (m, 2H), 0.81 (d, 6H, J=6.58 Hz).

The tosylate (7) was also prepared from acid (5) in an alternate method. This method was advantageous over the previous procedure above since it minimized the amount of β-isobutyl-γ-lactone produced as a by-product in the reaction above.

A solution of acid (5) (22.3 kg, 84.4 mol) in methyl-t-butyl ether (198 kg) was cooled to −6° C. Borane-methyl sulfide complex (15.6 kg, 177 mol) was added while maintaining a reaction temperature of 5° C. or less. The mixture was then warmed to 20° C. and stirred for two hours. The mixture was cooled to 0° C. and methanol (24 L) was added while maintaining a reaction temperature of SOC or less. Water (132 L) was added at a temperature of 150° C. or less. The phases were separated and the aqueous phase was extracted with methyl-t-butyl ether (27 kg). The organic were combined and extracted with water (72 L). The solution was concentrated to an oil by distillation and ethyl acetate (23 kg) was added. The solution was again concentrated to an oil by distillation to give alcohol (6). Pyridine (53 kg) was added. The solution was cooled to 1° C. and para-toluenesulfonyl chloride (23 kg, 121 mol) was added while maintaining a reaction temperature of −5° C. to 5° C. The mixture was stirred at 2° C. for 8 hours then warmed to 20° C. Water (12 L) was added while maintaining a reaction temperature of 23° C. or less. The mixture was cooled to 1°

C. and aqueous hydrochloric acid (52 kg concentrated acid in 63 L water) was added. Methyl-t-butyl ether (296 kg) was added and the mixture was warmed to 18° C. The phases were separated and the aqueous phase was extracted with methyl-t-butyl ether (74 kg). The organic phases were combined and extracted with aqueous hydrochloric acid (0.6 kg concentrated hydrochloric acid in 20 liters water), aqueous sodium bicarbonate (2.7 kg sodium bicarbonate in 50 liters water), and water (30 L). The organic solution was concentrated to an oil by distillation. Methyl-t-butyl ether (19 kg) was added and the mixture was again concentrated to an oil. The resulting product was dissolved in methyl-t-butyl ether (37.9 kg) and stored as a solution. Weight of tosylate (7) contained in methyl-t-butyl ether solution 30.1 kg (88% yield).

Step 7

A mixture of the tosylate (7) (14.44 g, 35.70 mmol) and sodium azide (5.50 g, 84.59 mmol) in 180 mL of anhydrous dimethylsulfoxide was heated at 65° C. overnight. The reaction mixture was cooled to room temperature and 900 mL of water was added. The mixture was extracted (4x) with a total of 2 L of hexanes. The combined organic extracts were dried with anhydrous magnesium sulfate and then filtered. The filtrate was concentrated and the resulting oil was then chromatographed by 8% ethyl acetate in hexanes on silica gel to give 8.55 g (87%) of the azide (8) as a colorless oil.

$^1$H NMR (300 MHz, CDCl$_3$): δ 7.37 (m, 5H) 5.14 (s, 2H), 3.33 (ABX, 2H, J$_{AB}$=12.27 Hz, J$_{AX}$=4.95 Hz, J$_{BX}$=6.10 HZ, υAB=22.87 Hz), 2.39 (m, 2H), 2.19 (m, 1H), 1.62 (m, 1H), 1.20 (m, 2H), 0.88 (d, 6H, J=6.44 Hz).

Step 8

To a solution of the azide (8) (8.55 g, 31.05 mmol) in 500 mL of tetrahydrofuran was added 62 mL of a 1N aqueous hydrochloric acid solution and 1 g of 10% palladium on carbon catalyst. The mixture was shaken overnight at room temperature on a Parr apparatus. The catalyst was removed by filtration over a pad of celte. The filtrate was concentrated and 50 mL of a 1N aqueous hydrochloric acid solution was added. The aqueous solution was wash ed with ether (3×50 mL). The aqueous layer was collected and then chromatographed on a Dowex 5W×8 (H$^+$ form) column eluted with a 0.5N aitmonium hydroxide solution. Fractions containing the amino acid (Ninhydrin positive) were collected and then lyophilized to give 3.2 g (65%) of the amino acid (9) as a white solid. mp=175–176° C.; [α]D$^{23}$ =10.520 (1.06, H$_2$O).

EXAMPLE 2

(S)-(+)-4-amino-3-c2-methylpropyl)butanoic acid

This compound was prepared in the same manner as Example 1, except that amino acid (9) is prepared from azide (8) by a 2 step process utilizing an intermediate azide (8a) which is subsequently reduced (the 1 step reduction approach identified as step 8 is described above). The synthetic procedure of Example 2 is depicted in Chart Ia.

Step 1: Preparation of Intermediate Azide (8a)

Azide (8) (10.7 g, 0.040 mol) in ethanol (100 mL) and water (20 mL) was treated with 50% aqueous sodium hydroxide (9.8 g). The mixture was stirred at 30° C. for 45 minutes. Ethanol was removed under reduced pressure until 30 g of liquid remained, water (100 mL) was added and the mixture was extracted with methyl-t-butyl ether (4×100 mL). The methyl-t-butyl ether extracts were extracted with 1 M sodium hydroxide and the aqueous phases were combined and acidified to pH 1.6 with concentrated hydrochloric acid. The aqueous mixture was then extracted with methyl-t-butyl ether (2×100 mL) and the organic extracts were combined and concentrated under reduced pressure. The resulting oil was dissolved in heptane (50 mL) and extracted with saturated aqueous sodium bicarbonate (2×40 mL). The aqueous extracts were extracted with heptane (50 mL), combined and acidified to pH 1.6 with concentrated hydrochloric acid. The aqueous mixture was extracted with heptane (2×50 mL). The heptane extracts were extracted with water (40 mL), combined, and concentrated under reduced pressure to give 5.4 g (75%) of intermediate azide (8a) as an oil.

$^1$H NMR (200 MHz, CDCl$_3$): δ 10.8 (br s, 1H), 3.36 (m, 2H), 2.38 (m, 2H), 2.18 (m, 1H), 1.64 (m, 1H), 1.25 (m, 2H), 0.91 (d, 6H, J=6.56 Hz).

Step 2: Synthesis of Amino Acid (9) from Intermediate Azide (8a)

Intermediate azide (8a) (12.7 g, 68.6 mol) was dissolved in methyl-t-butyl ether (80 kg). The mixture was subjected to catalytic hydrogenation in the presence of 5% palladium on carbon (2.0 kg of 50% water wet) at 49 to 55 psi of hydrogen until intermediate azide (8a) has been consumed. The mixture was filtered and the solid was washed with methyl-t-butyl ether (30 kg). The solid was dissolved in a solution of hot isopropanol (75 kg) and water (60 kg) and the solution was filtered. The isopropanol water solution was cooled to −3° C. and the product was filtered and washed with cold isopropanol (16 kg). The solid was dried under reduced pressure to give 6.4 kg (59%) of amino acid (9).

This reduction may be conducted in a variety of solvents. Successful reductions have been carried out in heptane, ethanol/water, isopropanol, isopropanol/water, methanol/water, and tetrahydrofuran/water as well as methyl-t-butyl ether.

(S)-(+)-4-amino-3-(2-methylpropyl)butanoic acid

The following "steps", refer to Chart II. All reactions were carried out under an atmosphere of nitrogen.

Step 1

To a solution of 4-methylvaleric acid (50.0 g, 0.43 mol) in 100 mL of anhydrous chloroform was added thionyl chloride (60 mL, 0.82 mol). The reaction mixture was refluxed for 2 hours and then cooled to room temperature. Excess chloroform and thionyl chloride was removed by distillation. The residue oil was then fractionally distilled to give 45.3 g (78%) of the acid chloride (102), bp=143–144° C.

Acid chloride (102) was also prepared by an alternative method which eliminated use of chloroform which has waste disposal and operator exposure difficulties. The alternate method also minimized the formation of 4-methylvaleric anhydride.

To a solution of thionyl chloride (98.5 kg, 828 mol) and N,N-dimethylformamide (2 kg, 27 mol) was added 4-methylvaleric acid (74 kg, 637 mol) while maintaining a reaction temperature of 25–30° C. Hexanes (30 L) were added and the solution was maintained at 30° C. to 35° C. for 1 hour and 15 minutes. The solution was then heated to 70° C. to 75° C. for 1 hour and 10 minutes. The solution was subjected to atmospheric distillation until a solution temperature of 95° C. was reached. After cooling, hexanes (30 L) were added and the solution was subjected to atmospheric distillation until a solution temperature of 97° C. was reached. Distillation of the residual oil produced 79 kg (92%) of acid chloride (102), bp=−77° C., 60–65 mm Hg.

Step2

To a solution of (4R,5S)-(+)-4-methyl-5-phenyl-2-oxazolidinone (5.27 g, 29.74 mmol) in 70 mL of anhydrous tetrahydrofuran at −78° C. under argon atmosphere was added a 1.6 M solution of n-butyllithium (19 mL, 30.40 mmol) in hexanes slowly. The mixture was allowed to stir at −78° C. for 15 minutes then the acid chloride (4.5 g, 33.43 mmol) was added to quench the reaction. The reaction was stirred at −78° C. for 10 minutes then 0° C. for 30 minutes. A saturated solution of sodium bicarbonate (50 mL) was added and the mixture was stirred at 0° C. for 30 minutes. The organic layer was collected and the aqueous layer was extracted with ethyl acetate (3×). The organic extracts were combined and dried with anhydrous magnesium sulfate. It was then filtered and concentrated to give a colorless oil. The oil was then chromatographed with 8% ethyl acetate in hexanes on silica gel to give 7.56 g (82%) of the acyloxazolidinone (103) as a white solid.

Anal. Calcd for $C_{16}H_{21}NO_3$: C, 69.79; H, 7.69; N, 5.09. Found: C, 69.56; H, 7.63; N, 5.06.

Acyloxazolidinone (103) was also prepared by an alternate method which was conducted at −5° C. to 0° C. rather than −78° C. which is difficult and expensive to achieve on a manufacturing scale. The alternate method also gave a crystalline solid from the reaction mixture rather than an oil which must be chromatographed.

To a solution of 4-methyl-5-phenyl-2-oxazolidinone (64 g, 0.36 mol) in anhydrous tetrahydrofuran (270 g) at −5° C. was added a 15% solution of n-butyllithium in hexane (160 g, 0.37 mol) over a temperature range of −5° C. to 0° C. Acid chloride (102) (48.6 g, 0.36 mol) was added at −10° C. to 0° C. The reaction was quenched with a solution of water (90 mL) and sodium bicarbonate (4 g). Ethyl acetate (200 g) was added and the layers were separated. The organic layer was extracted with water (2×50 mL) and the aqueous phases were back extracted with ethyl acetate (100 g). The organic extracts were combined and approximately 150 mL of solvent was removed by distillation. Atmospheric distillation was continued and heptane (2×200 g) was added until a vapor temperature of 95° C. was reached. The solution was cooled to 5° C. The product was collected by filtration, washed with cold heptane, and dried to give 79 g (80%) of acyloxazolidinone (103),.

Step 3

To a solution of diisopropylamine (7.6 g, 0.075 mol) in anhydrous tetrahydrofuran (10 mL) at 0° C. under nitrogen was added a 1.6 M n-butyllithium in hexane (47 mL, 0.075 mol) while maintaining a temperature of −5° C. to 0° C. The resulting solution was added to a solution of acyloxazolidinone (103) (18.6 g, 0.068 mol) in tetrahydrofuran (160 mL) at −55° C. to −45° C. The solution was stirred at −55° C. to −45° C. for 30 minutes. The solution was then added to a solution of t-butyl bromoacetate (14.6 g, 0.075 mol) in tetrahydrofuran at −55° C. to −45° C. The solution was cooled to −65° C. and allowed to warm to 10° C. over a period of 2 hours. The reaction mixture was quenched with the addition of saturated aqueous ammonium chloride and extracted with ethyl acetate. The organic layer was dried (MgSO$_4$), filtered, and the solvent was removed under reduced pressure. The residue was recrystallized from heptanes, filtered, and dried under reduced pressure to give 18 g (68%) of acyloxazolidinone (104).

$^1$H NMR (200 MHz, CDCl$_3$): δ 7.4–7.2 (m, 5H), 5.65 (d, 1H, J=7.09 Hz), 4.74 (m, 1H), 4.26 (m, 1H), 2.69 (m, 1H), 2.44 (m, 1H), 1.65–1.45 (m, 2H), 1.39 (s, 9H), 0.93 (m, 6H), 0.89 (d, 3H, J=7.87 Hz).

Alternatively, the order of addition of the reagents may be reversed. t-Butyl bromoacetate may be added to the solution containing diisopropylamine, n-butyllithium and acyloxazolidinone (103). The final product isolation may also be conducted by doing a distillation and replacing the solvents present (hexane and tetrahydrofuran) with isopropyl alcohol. Acyloxazolidinone (104) then crystallizes from the isopropyl alcohol solution. The following experimental procedure illustrates this alternative.

To a solution of diisopropylamine (23.1 g, 0.229 mol) in anhydrous tetrahydrofuran (30 mL) at 0° C. under nitrogen was added a 2.5 M n-butyllithium in hexane (92 mL, 0.229 mol) while maintaining a temperature of −5° C. to 0° C. The resulting solution was added to a solution of acyloxazolidinone (103) (60.0 g, 0.218 mol) in tetrahydrofuran (400 mL) at −45° C. to 40° C. The solution was stirred at −45° C. to −40° C. for 30 minutes. t-Butyl bromoacetate (44.6 g, 0.229 mol) was then added to the reaction solution at −45° C. to −40° C. The solution was allowed to warm to 10° C. over a period of 2 to 3 hours. The reaction mixture was quenched with the addition of saturated aqueous ammonium chloride. The organic layer was separated from the water layer. The solvent was removed under reduced pressure and replaced with isopropyl alcohol. The product crystallized from isopropyl alcohol and was filtered and dried under reduced pressure to give 53.8 g (63%) of acyloxazolidinone (104).

Step 4

To a precooled (5° C.) solution of acyloxazolidinone (104) (60.0 g, 0.15 mol) in tetrahydrofuran (266 g) was added a solution of 30% hydrogen peroxide (71 g), 9.4 g lithium hydroxide monohydrate (0.22 mol) and water (120 mL) over a period of 35 minutes so as to maintain a reaction temperature of 5° C. The mixture was stirred at 3–5° C. for 2.5 hours. The reaction was quenched by addition of a solution of sodium sulfite (50 g), sodium bisulfite (27 g), and water (310 mL) at a temperature of less than 29° C. Heptane (100 mL) and methyl-t-butyl ether (100 mL) were added and the layers were separated. The aqueous layer was extracted with methyl-t-butyl ether (100 mL) and the organic layers were combined. The solvent was replaced with heptane by distillation and the resulting heptane solution (400 mL) was cooled to 5° C. The resulting solids were filtered and the filtrate was extracted with warm water (2×150 mL, 1×200 ml, 1×300 mL). The solution was concentrated by evaporation to give 34.5 g (97%) acid (105) as an oil.

$^1$H NMR (200 MHz, CDCl$_3$): δ 11.5 (br, s, 1H), 2.85 (m, 1H), 2.67–2.29 (m, 2H), 1.60 (m, 1H), 1.44 (s, 9H), 1.32 (m, 2H), 0.92 (m, 6H).

Step 5

Acid (105) (72.4 g, 0.314 mol) was dissolved in tetrahydrofuran (360 mL) and cooled to 0° C. A 2.0 M solution of borane dimethylsulfide complex in tetrahydrofuran (178 mL, 0.356 mol) was added at 0° C. The solution was allowed to warm to 48° C. then cooled to 25° C. After 2 hours and 45 minutes, the reaction was quenched with the addition of methanol (300 mL) and the solvent was removed under reduced pressure. Additional methanol (300 mL) was added and the solution was concentrated under reduced pressure to give 66 g (97%) of alcohol (106) as an oil.

$^1$H NMR (500 MHz, CDCl$_3$): δ 3.62 (m, 1H), 3.45 (m, 1H), 2.44 (br s, 1H), 2.36–2.21 (m, 2H), 2.05 (m, 1H), 1.64 (m, 1H), 1.45 (s, 9H), 1.24–1.04 (m, 2H), 0.91 (m, 6H).

Step 6

Alcohol (107) (51.9 g, 0.24 mol) was dissolved in pyridine (130 ml) and cooled to 5° C. p-Toluene sulfonyl chloride (57.2 g, 0.30 mol) was added and the mixture was stirred at 22° C. for 21 hours. The reaction was quenched with the addition of water (95 mL) and 18% aqueous hydrochloric acid (300 mL) at less than 300° C. Methyl-t-butyl ether (350 mL) was added and the layers were separated. The aqueous layer was extracted with methyl-t-butyl ether (350 mL). The organic layers were combined, washed with 1% aqueous hydrochloric acid (2×100 mL), saturated aqueous sodium bicarbonate (1×150 mL), and water (1×100 mL). The organic solution was treated with decolorizing charcoal, filtered, and evaporated to give 77 g (86%) of the tosylate (107) as an oil.

$^1$H NMR (200 MHz, CDCl$_3$): δ 7.78 (d, 2H, J=8.25 Hz), 7.34 (d, 2H, J=8.25 Hz), 3.96 (m, 2H), 2.45 (s, 3H), 2.32–2.12 (m, 3H), 1.6–1.4 (m, 1H), 1.40 (s, 9H), 1.2–1.1 (m, 2H), 0.83 (m, 6H).

Step 7

Tosylate (107) (65 g, 0.175 mol) was dissolved in dimethyl sulfoxide (40 mL). The dimethyl sulfoxide solution along with additional dimethyl sulfoxide (10 mL) was than added to a solution of sodium azide (11 g, 0.26 mol) in dimethyl sulfoxide (450 g) at 63° C. The mixture was then stirred at 65° C. for 6 hours. Water (140 mL) and heptane (250 mL) were added to the reaction and the layers were separated. The aqueous layer was extracted with heptane (250 mL) and the organic layers were combined. The solvent was removed under reduced pressure to give 42 g (95%) of the azide (108) as an oil.

$^1$H NMR (200 MHz, CDCl$_3$): δ 3.32 (m, 2H), 2.22 (m, 2H), 2.15 (m, 1H), 1.63 (m, 1H), 1.46 (s, 9H), 1.19 (m, 2H), 0.89 (m, 6H).

Step 8

Azide (108) (36.3 g, 0.15 mol) was placed in 88% aqueous formic acid (365 mL). The mixture was stirred at 30° C. for 4.5 hours. Decolorizing charcoal was added and the mixture was filtered and concentrated under reduced pressure to give an oil. Heptane (250 mL) was added and the mixture was vacuum distilled to give an oil. Water (125 mL) and heptane (250 mL) were added and mixed vigorously. The layers were separated and the water layer was washed with heptane (250 mL). The heptane layers were combined and concentrated under reduced pressure to give 24.6 g (88%) of intermediate azide (108a) as an oil.

Alternatively, aqueous hydrochloric acid may be used rather than aqueous formic acid in order to conduct the hydrolysis.

Step 9

Intermediate azide (108a) (12.7 g, 68.6 mol) was dissolved in methyl-t-butyl ether (80 kg). The mixture was subjected to catalytic hydrogenation in the presence of 5% palladium on carbon (2.0 kg of 50% water wet) at 49–55 psi of hydrogen until intermediate azide (108a) has been consumed. The mixture was filtered and the solid was washed with methyl-t-butyl ether (30 kg). The solid was dissolved in a solution of hot isopropanol (75 kg) and water (60 kg) and the solution was filtered. The isopropanol water solution was cooled to −3° C. and the product was filtered and washed with cold isopropanol (16 kg). The solid was dried under reduced pressure to give 6.4 kg (59%) of amino acid (109).

This reduction may be conducted in a variety of solvents. Successful reductions have been carried out in heptane, ethanol/water, isopropanol, isopropanol/water, methanol/water, and tetrahydrofuran/water as well as methyl-t-butyl ether.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

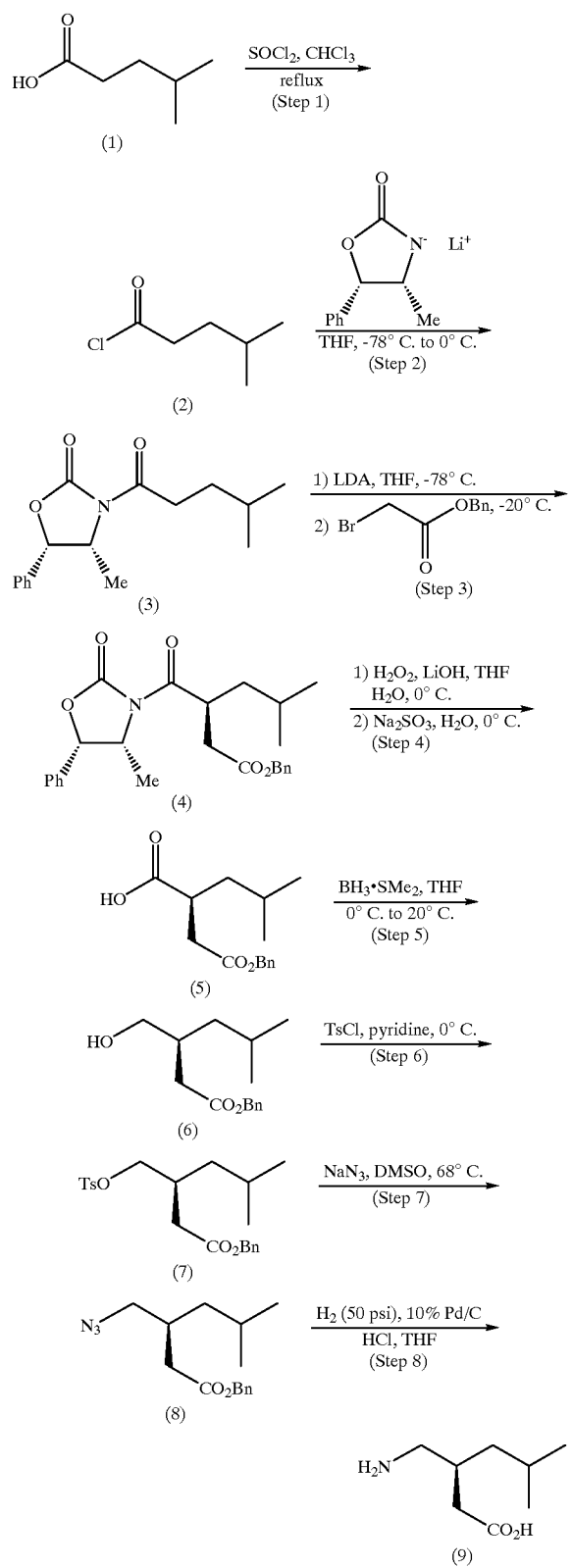

CHART I

CHART Ia
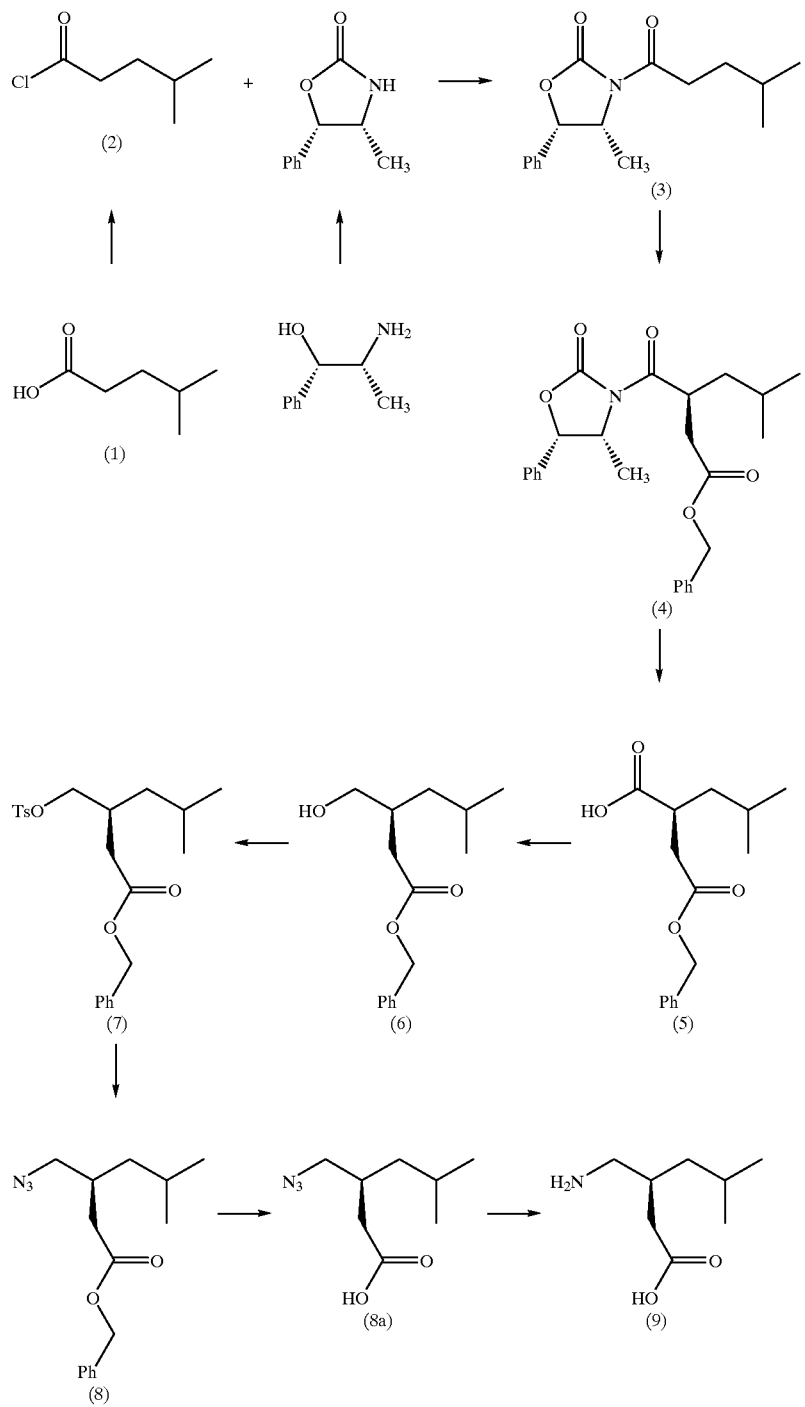

CHART II

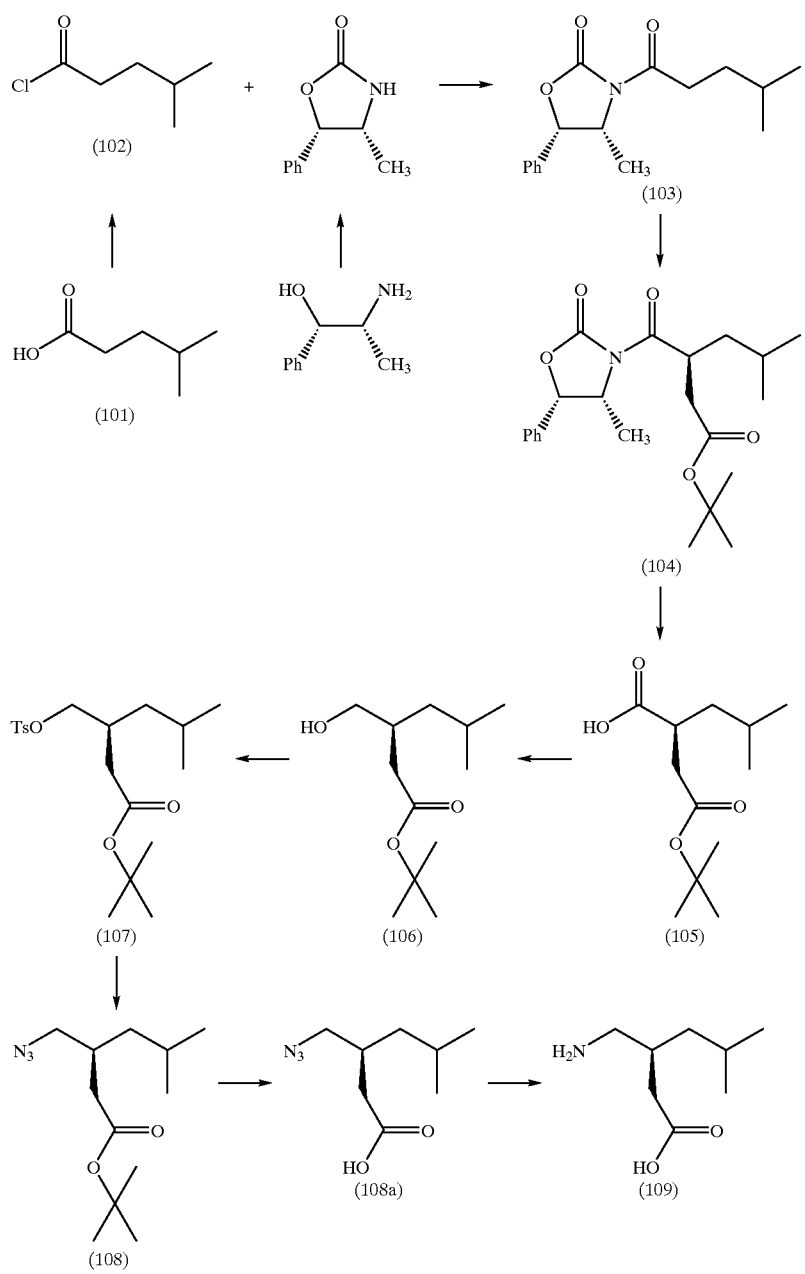

What is claimed is:

1. A method of treating a patient having Parkinson's Disease which includes administering to a patient an anti-seizure effective amount of the compound 4-amino-3-(2-methylpropyl) butanoic acid.

2. A method of treating a patient having Parkinson's Disease which includes administering to a patient an anti-seizure effective amount of the compound S-(+)-4-amino-3-(2-methylpropyl) butanoic acid.

* * * * *

UNITED STATES PATENT AND TRADEMARK OFFICE
CERTIFICATE OF CORRECTION

PATENT NO. : 6,291,526 B1
DATED : September 18, 2001
INVENTOR(S) : Richard B. Silverman et al.

It is certified that error appears in the above-identified patent and that said Letters Patent is hereby corrected as shown below:

<u>Column 1,</u>
Lines 18-21, replace with the following, -- GRANT INFORMATION: Research in this application was supported in part by a grant from the National Institute of Health (NIH Grant No. NS15703). The Government has certain rights in the invention.

Signed and Sealed this

First Day of July, 2003

JAMES E. ROGAN
*Director of the United States Patent and Trademark Office*